United States Patent
Kim et al.

[11] Patent Number: 5,872,254
[45] Date of Patent: Feb. 16, 1999

[54] WHITENING COSMETICS CONTAINING RAMULUS MORI EXTRACTS

[75] Inventors: Jeong-Ha Kim, Seoul; Kang-Tae Lee, Chungcheongnam-do, both of Rep. of Korea

[73] Assignee: Coreana Cosmetics Co., Ltd., Rep. of Korea

[21] Appl. No.: 986,840

[22] Filed: Dec. 8, 1997

[30] Foreign Application Priority Data

Feb. 18, 1997 [KR] Rep. of Korea ............... 1997 4913
Sep. 12, 1997 [KR] Rep. of Korea ............. 1997 47258

[51] Int. Cl.$^6$ ......................................... C07D 211/36
[52] U.S. Cl. ............................................... 546/242
[58] Field of Search ........................................... 546/242

[56] References Cited

U.S. PATENT DOCUMENTS 4,137,231  1/1979  Murai et al. ..................... 546/242

OTHER PUBLICATIONS

Heterocycles, vol. 15, No. 2, 1981; pp. 1531–1567; Taro Nomura, et al. "Prenylflavonoids from the root back of the cultivated mulberry tree".

Cosmetics & Toiletries magazine; vol. 111, Oct. 1996; pp. 65–77; "Skin Lightners".

Cosmetics & Toiletries magazine; vol. 107, Nov. 1992; pp. 61–68; Pawelek, et al.; "Ultraviolet Light and Pigmentation of the Skin".

Cosmetics & Toiletries magazine, vol. 112, Mar, 1997; pp. 59–62; Jang, et al.; "Melanogenesis Inhibitor from Paper Mulberry".

International Journal of Cosmetic Science 19, 000–000 (1997); pp. 1–7; Lee, et al.; "Biological screening of 100 plant extracts for cosmetic use (I): inhibitory activities of tyrosinase and DOPA auto–oxidation".

Chem. Pharm.Bull 25(3) pp. 529–532 (1977); "Kuwanon A,B,C and Oxydihydromorusin, Four New Flavones from the Root Bark of the Cultivated Mulberry Tree".

Heterocycles, vol. 14, No. 12, 1980; pp. 1943–1951; Taro Nomura, et al.; "Hypotensive constituent, kuwanon H, a new flavone derivative from the rootbark of the cultivated mulberry tree".

J. Soc. Cosmet. Chem., 42, 361–368 (Nov./Dec. 1991); Kazuhisa Maeda, et al.; "In vitro effectiveness of several whitening cosmetic components in human melanocytes".

*Primary Examiner*—Terressa Mosley
*Attorney, Agent, or Firm*—Nields, Lemack & Dingman

[57] ABSTRACT

The present invention relates to cosmetics having whitening effect, which contains ramulus mori extracts. The invention provides cosmetics showing excellent whitening effect prepared by adding extracts obtained by acting ramulus mori (dried young twigs of plants belonged to Morus Genus) with water, absolute or aqueous lower alcohol containing 1~4 carbons, acetone, ethyl acetate, butyl acetate, chloroform or 1,3-butylene glycol, to a conventional skin-care cosmetic product such as skin softener, nutrient emulsion (milk lotion), nutrient cream, massage cream, essence and facial pack.

7 Claims, 1 Drawing Sheet

WHITENING COSMETICS CONTAINING RAMULUS MORI EXTRACTS

FIELD OF THE DEVICE

The present invention relates to cosmetic products having whitening effect, which contains ramulus mori extracts that is extracted from young twig of plants belonged to *Morus Genus*.

PRIOR ARTS

In general, there are various reasons for the darkening of skin color. And the main reason is ultraviolet radiation. When skin is exposed to ultraviolet ray, melanin is synthesized in melanocytes, which is a kind of skin cells, and released to darken skin color. In the process of melanin synthesis in melanocytes, tyrosinase reacts on tyrosine, which is a substrate for tyrosinase in the cell to yield DOP Aquinone and it goes through spontaneous reaction and enzyme reaction to synthesize a copolymeric black pigment, melanin. Thus, to prevent darkening of skin color, it is most simple and general to inhibit a part of the process of melanin biosynthesis, and reduce the production of melanin.

For this reason, ascorbic acid, kojic acid, arbutin, hydroquinone or plant extracts like cortex mori extracts have been conventionally used as whitening agent up to the present.

Among these, kojic acid forms a chelate with a copper ion which is present at the active site of tyrosinase and it inhibits the enzyme activity. Though it has high activity, it is not appropriate to be used in cosmetics because of its stability problem.

Ascorbic acid cannot be properly used as a whitening agent because it has relatively low activity of inhibiting tyrosinase and low stability of the molecule itself.

Hydroquinone irritates the skin strongly, so that it is not used as a cosmetic material in these days for its safety problem.

Most of plant extracts can reveal substantial inhibition effect on tyrosinase activity, only if they are used in a high concentration. When they are used in a low concentration, the inhibiting activity hardly occurs.

SUMMARY OF THE INVENTION

The present inventors have paid attention to these circumstances and performed intensive studies for finding more excellent whitening agent which does not involve the problems of conventional whitening agent. As a result of searching for effective material having whitening activity among the natural plants of which the safety has been already proved as they have been used in herb remedies or folk remedies for a long time, the inventors found that the extracts of ramulus mori, young twigs of plants belonged to *Morus Genus,* showed excellent inhibiting activity on tyrosinase.

The object of the present invention is to provide whitening cosmetics containing ramulus mori extracts.

More specifically, it is to provide cosmetics showing excellent whitening effect prepared by adding, to a conventional skin-care cosmetic product, the extracts of ramulus mori extracted with water, absolute or aqueous lower alcohol containing 1~4 carbons, acetone, ethyl acetate, butyl acetate, chloroform or 1,3-butylene glycol.

DETAILED DESCRIPTION OF THE INVENTION

Figure 1:
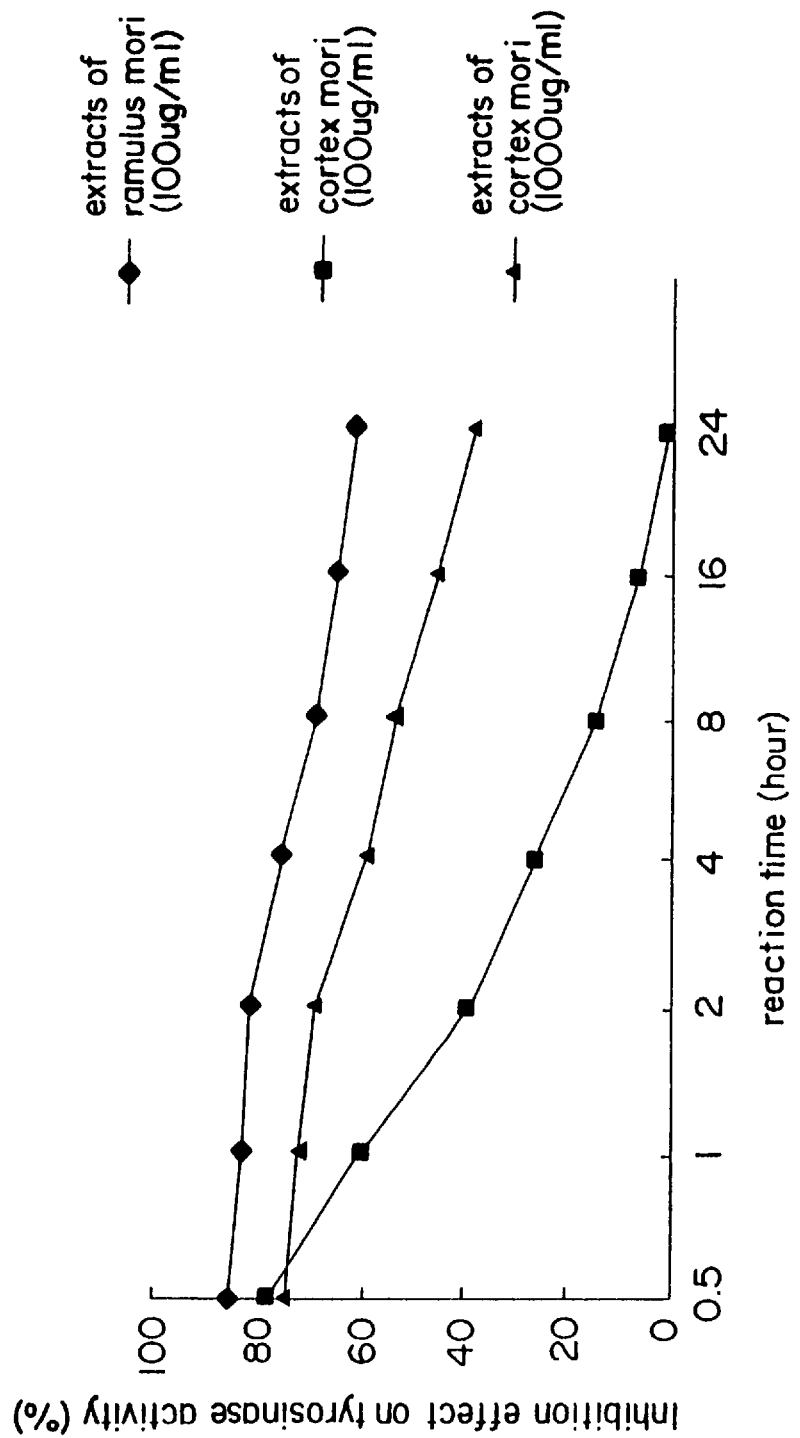
FIG. 1 shows the maintenance of the inhibition effect on tyrosinase activity of ramulus mori extracts according to the present invention as compared to that of cortex mori extracts.

Now, the present invention is described in more detail.

*Morus Genus* includes Morus alba, Linne; Morus alba for. Pelldullus DIPPEL; Morus bombycis, Koidzumi; Morus bombycis var. Caudatifolia; Morus bombycis var. maritima KOIDZ; Morus bombycis for. Kase VYKEI; Morus tiliaefolia, Makino; and so on. These plants are tall trees of broad-leaved larch, widely distributed in Korean peninsula at a level of 500~1400m of altitude and grow spontaneously around mountain villages or at the feet of mountains.

Ramulus mori is dried young twig of plants belong to *Morus Genus*. The shape is like a long cylinder having side twigs sparsely. The size is not regular, but the diameter is about 0.5~1.5cm. The surface is greyish yellow or yellowish brown with lots of yellowish brown dot-like skin holes and minute seed-out and with greyish white semicircular signs of leaves and yellowish brown axillary buds. The thickness of the cut piece is about 0.2~0.5cm. The piece has relatively thin exodermis part and yellowish white woody part. The oblique line is radial and the head part is white or yellowish white. The gathering season is desirable between late spring and early summer. After removing the leaves, the twigs are cut in a length of 30~60 cm when they are still fresh, and dried under sunlight. Ramulus mori has somewhat bitter taste. And due to its activities of antiphlogistic, diuresis, invigorant, diaphoretic and alleviating paralysis, it has been used as a material of Chinese medicine from olden times.

The process for preparation of ramulus mori extracts used in the whitening cosmetics according to the present invention is as follows:

Ramulus mori is washed with distilled water and cut into small pieces. And then, it is added a solvent (such as water, absolute or aqueous lower alcohol containing 1~4 carbons, acetone, ethyl acetate, butyl acetate, chloroform or 1,3-butylene glycol) of one to ten weight folds of the dried pieces. The mixture is extracted by heating at 40°–100° C. for 3~20 hours with an equipment of condenser to prevent the evaporation of active components, or at 4°~40° C. for 1~15 days. Then, the solvent of the extracts is completely evaporated to dryness by the use of a rotary evaporator.

The ramulus mori extracts thus prepared is added to conventional skin-care cosmetics such as skin softener (skin lotion), nutrient emulsion (milk lotion), nutrient cream, massage cream, essence and facial pack. The amount of the extracts added is about 0.00001~5% (w/w), preferably 0.001~1% (w/w), based dry weight of each.

The whitening effect of the ramulus mori extracts according to the present invention has been compared with that of conventional whitening agent such as extracts of cortex mori, licorice root, galla rhois, paeoniae radix and sophora japonica. As a result, ramulus mori extracts according to the present invention showed most excellent inhibition effect on tyrosinase activity. Thus, ramulus mori extracts is proved to be excellent whitening agent. In particular, ramulus mori extracts exhibits quite excellent retentive whitening effect as compared to that of cortex mori extracts. More then ten-fold concentration of cortex mori extracts, on the basis of ramulus mori extracts, showed the same retentive inhibition effect on tyrosinase activity as that of ramulus mori extracts. Though both ramulus mori and cortex mori are natural products originated from mulberry trees and both show the inhibition effect on tyrosinase activity, two extracts showed quite different components from chemical analysis and ramulus mori extracts showed much better whitening effect.

PREFERRED EMBODIMENTS OF THE INVENTION

Now, The present invention is described with reference to Examples and Experimental Examples. However, it should not be noted that the present invention is restricted to those examples.

EXAMPLE 1

Ramulus mori (1 kg), which had been washed with distilled water and dried, was added to water (5 L) and extracted by heating in an extractor equipped with a condenser at 70°~90° C. for 5 hours. The resultant material was filtered through 300 mesh filtering cloth and stood at 5°~10° C. for 7~10 days for aging. Then the material was filtered through a filter paper of Whatman No. 5. The filtrate was concentrated to dryness by using rotary evaporator at 65° C. to give the dry extracts (dry weight: 40.4 g).

EXAMPLE 2

Ramulus mori (1 kg), which had been washed with distilled water and dried, was added to water (5 L) and extracted at 15°~35° C. for 5 days. TfIhe resultant material was filtered through 300 mesh filtering cloth and then through a filter paper of Whatman No. 5. The filtrate was concentrated twice by using rotary evaporator. Absolute ethanol (100%, 2.5 L) was added thereto and the mixture was stood at 5°~10° C. for 7~10 days for aging. Then, the mixture was filtered through a filter paper of Whatman No. 5. The filtrate was concentrated to dryness by using rotary evaporator at 65° C. to give the dry extracts (dry weight: 32.5 g).

EXAMPLE 3

Ramulus mori (1 kg), which had been washed with distilled water and dried, was added to water (5 L) and extracted at 4°~40° C. for 5 days. The resultant material was filtered through 300 mesh filtering cloth and stood at 5°~10° C. for 7~10 days for aging. Then the material was filtered through a filter paper of Whatman No. 5. The filtrate was concentrated to dryness by using rotary evaporator at 65° C. to give the dry extracts (dry weight: 33.6 g).

EXAMPLE 4~22

Ramulus mori was extracted according to the same procedure as Example 3 and the results are recorded in Table 1.

TABLE 1

Experimental Results of Example 4 ~ 22

| | Extraction solvent | Dry weight of final extract (unit:g) |
|---|---|---|
| Example 4 | 10% ethanol | 43.84 |
| Example 5 | 20% ethanol | 46.80 |
| Example 6 | 30% ethanol | 39.24 |
| Example 7 | 40% ethanol | 39.52 |
| Example 8 | 50% ethanol | 48.96 |
| Example 9 | 60% ethanol | 48.72 |
| Example 10 | 70% ethanol | 50.08 |
| Example 11 | 80% ethanol | 41.64 |
| Example 12 | 90% ethanol | 35.76 |
| Example 13 | 100% ethanol | 28.90 |
| Example 14 | methanol | 46.16 |
| Example 15 | n-propanol | 10.28 |
| Example 16 | iso-propanol | 10.45 |
| Example 17 | 2-butanol | 16.45 |
| Example 18 | acetone | 6.57 |
| Example 19 | chloroform | 3.31 |
| Example 20 | ethyl acetate | 10.91 |
| Example 21 | butyl acetate | 6.61 |
| Example 22 | 1,3-butylene glycol | 12.31 |

EXAMPLE 23

Ramulus mori (1 kg), which had been washed with distilled water and dried, was added to 10% ethanol (5 L) and extracted by heating in an extractor equipped with a condenser for 5 hours. The resultant material was filtered through 300 mesh filtering cloth and stood at 5°~10° C. for 7~10 days for aging. Then the material was filtered through a filter paper of Whatman No. 5. The filtrate was concentrated to dryness by using rotary evaporator at 65° C. to give the dry extracts (dry weight: 59.40 g).

EXAMPLE 24~32

Ramulus mori was extracted according to the same procedure as Example 23, and the results are recorded in Table 2.

TABLE 2

Experimental Results of Example 24 ~ 32

| | extraction solvent | dry weight of final extract (unit:g) |
|---|---|---|
| Example 24 | 20% ethanol | 63.42 |
| Example 25 | 30% ethanol | 58.15 |
| Example 26 | 40% ethanol | 59.54 |
| Example 27 | 50% ethanol | 66.60 |
| Example 28 | 60% ethanol | 67.24 |
| Example 29 | 70% ethanol | 68.77 |
| Example 30 | 80% ethanol | 58.30 |
| Example 31 | 90% ethanol | 50.06 |
| Example 32 | 100% ethanol | 44.17 |

EXPERIMENTAL EXAMPLE 1

The tyrosinase inhibition effect of each ramulus mori extracts obtained from Examples 1~32 was determined.

A tyrosinase, commercially available one from Sigma Co. which had been separated from mushroom and distilled, was used. The substrate, tyrosine was used as a solution (0.1 mg/ml) dissolved in 0.05M sodium phosphate buffer (pH 6.8).

Each extracts obtained from Examples 1~32 was dissolved in 1,3-butylene glycol at a high concentration, and the solution was further diluted to an appropriate concentration with the buffer solution, to give an extracts sample.

Tyrosine solution (0.5 ml) was placed in a test tube and the extracts sample (0.5 ml) was added thereto. The test tube was stood in an incubator at 37° C. for 10 minutes, and then 200 U/ml tyrosinase (0.5 ml) was added thereto. The reaction was carried out at the same temperature for 10 minutes. As a control group, buffer solution (0.5 ml) was added instead of each extracts. The reaction was quenched by placing the test tube on ice to inhibit more reaction in the system. Absorbance was measured at a wavelength of 475 nm by using a spectrophotometer.

The inhibition effects of each extracts on tyrosinase activity was determined by the equation below:

Inhibition ratio of tyrosinase activity (%)=100−(100× Absorbance of each extracts/Absorbance of control group)

The results are shown in Table 3.

TABLE 3 inhibition effect of ramulus mori extracts on tyrosinase activity

| Test material | Concentration of final test (% W/V) | Inhibition ratio of tyrosinase activity (%) |
|---|---|---|
| Example 1 | 0.00050 | 66.6 |
| Example 2 | 0.00050 | 91.7 |

TABLE 3-continued inhibition effect of ramulus mori extracts on tyrosinase activity

| Test material | Concentration of final test (% W/V) | Inhibition ratio of tyrosinase activity (%) |
| --- | --- | --- |
| Example 3 | 0.00050 | 42.2 |
| Example 4 | 0.00050 | 25.6 |
| Example 5 | 0.00050 | 29.3 |
| Example 6 | 0.00050 | 54.2 |
| Example 7 | 0.00050 | 69.6 |
| Example 8 | 0.00050 | 89.8 |
| Example 9 | 0.00050 | 96.7 |
| Example 10 | 0.00050 | 99.4 |
| Example 11 | 0.00050 | 96.5 |
| Example 12 | 0.00050 | 90.3 |
| Example 13 | 0.00050 | 89.5 |
| Example 14 | 0.00050 | 95.2 |
| Example 15 | 0.00050 | 83.4 |
| Example 16 | 0.00050 | 95.4 |
| Example 17 | 0.00050 | 92.9 |
| Example 18 | 0.00050 | 97.6 |
| Example 19 | 0.00050 | 68.5 |
| Example 20 | 0.00050 | 96.4 |
| Example 21 | 0.00050 | 93.2 |
| Example 22 | 0.00050 | 71.6 |
| Example 23 | 0.00050 | 42.6 |
| Example 24 | 0.00050 | 68.8 |
| Example 25 | 0.00050 | 89.2 |
| Example 26 | 0.00050 | 92.1 |
| Example 27 | 0.00050 | 96.7 |
| Example 28 | 0.00050 | 98.6 |
| Example 29 | 0.00050 | 99.1 |
| Example 30 | 0.00050 | 99.0 |
| Example 31 | 0.00050 | 97.6 |
| Example 32 | 0.00050 | 95.3 |

COMPARATIVE EXAMPLE 1~5

Cortex mori (Comparative Example 1), licorice root (Comparative Example 2), galla rhois (Comparative Example 3), paeoniae radix (Comparative Example 4) or sophora japonica (Comparative Example 5) (each 1 kg), which had been washed with distilled water and dried, was extracted according to the procedure of Example 10 to obtain dry extracts.

EXPERIMENTAL EXAMPLE 2: COMPARISON OF TYROSINASE INHIBITION EFFECT: RAMULUS MORI EXTRACTS VS. OTHER EXTRACTS FROM NATURAL PRODUCTS SUCH AS CORTEX MORI

Ramulus mori extracts prepared in Example 10 was used inhibition effect of tyrosinase activity depending on the concentration of extracts prepared in Comparative Examples 1~5 and ramulus mori extracts were measured according to the same procedure of Experimental Example 1. The inhibition effect of ramulus mori extracts was compared to those of extracts of conventional whitening agents, i. e., cortex mori, licorice root, galla rhois, paeoniae radix or sophora japonica.

The results are shown in Table 4.

TABLE 4

Tyrosinase inhibition effect of ramulus mori extracts and other extracts of natural products

| Test material | $IC_{50}$:μg/ml (Concentration required for 50% inhibition of tyrosinase activity) |
| --- | --- |
| Example 10 | 12.48 |
| Comparative example 1 | 16.62 |
| Comparative example 2 | 71.00 |
| Comparative example 3 | 28.05 |
| Comparative example 4 | 269.24 |
| Comparative example 5 | 93.42 |

As can be shown from the above results, ramulus mori extracts showed excellent tyrosinase inhibition effect of the extracts and excellent whitening effect as compared to extracts of other natural products such as cortex mori.

EXPERIMENTAL EXAMPLE 3: COMPARISON OF MAINTENANCE OF TYROSINASE INHIBITION EFFECT OF RAMULUS MORI EXTRACTS AND CORTEX MORI EXTRACTS

In order to examine whether ramulus mori extracts and cortex mori extracts exhibit maintained whitening effect, the reaction mixture containing the extracts was kept at 37° C. according to Experimental Example 1, and the inhibition effect of tyrosinase activity was measured with the lapse of time.

Ramulus mori extracts prepared according to Example 8, and cortex mori extracts prepared according to Comparative Example 1 were used.

The results are illustrated in FIG. 1.

The result shows that ramulus mori extracts exhibits quite excellent retentive whitening effect as compared to that of cortex mori extracts. More than ten-fold concentration of cortex mori extracts, on the basis of ramulus mori extracts, showed the same retentive inhibition effect on tyrosinase activity as that of ramulus mori extracts.

EXPERIMENTAL EXAMPLE 4: COMPARISON OF RAMULUS MORI EXTRACTS VS. CORTEX MORI EXTRACTS FOR MELANIN SYNTHESIS IN MELANOCYTES

As melanocytes, commercially available B-16 melanoma (ATCC CRL 6323) cell line derived from mouse was used.

The melanoma cell line was inoculated in DMEM culture medium containing glucose (4.5 g/l), 10% serum and 1% antibiotic agent, and cultivated in a 50 ml T-flask at 37° C. After cultivating under a condition of 5% $C_2O_2$ for 24 hours, the culture solution was treated with 0.05% trypsin containing 0.02% EDTA to isolate cells, which was then inoculated in a 50 ml T-flask and cultivated for 48 hours. At this time, the number of cells was $4.57 \times 10^6$ cells/flask. A diluted solution of ramulus mori extracts in DMEM medium at a proper concentration was incorporated to the cultivated melanoma cells, and the mixture was cultivated at 37° C. for 5 days. After finishing cultivation, culture medium was thoroughly removed, and the residue was treated with 1 ml of saline-phosphate buffer solution (PBS) containing 0.02% EDTA and 0.05% trypsin to isolate cells, which were then centrifuged for 5 minutes to collect pure cells. The obtained cells were treated with a solution of 5% trichloroacetate (TCA), stirred, and centrifuged. Precipitated melanin was washed with saline-phosphate buffer solution, and treated with 1N NaOH to dissolve melanin therein. Absorbance at 475 nm was measured. Melanin concentration was determined from standard concentration curve of synthetic melanin (produced by Sigma Co.).

The results are shown in Table 5.

TABLE 5

Comparison of ramulus mori extracts and cortex mori extracts melanin synthesis in melanocytes.

| Concentration of extract (μg/ml) | Inhibiting ratio on melanin syntheses (%) | |
|---|---|---|
| | Ramulus mori extracts | Cortex mori extracts |
| 50 | 73.1 | 1.1 |
| 100 | 85.2 | 3.8 |
| 150 | 89.7 | 20.1 |
| 200 | 90.2 | 29.4 |

Thus, the ramulus mori extracts comparing to cortex mori extracts is a strong whitening agent inhibiting melanin synthesis in melanocytes.

EXPERIMENTAL EXAMPLE 5: COMPARISON OF COMPONENTS BETWEEN RAMULUS MORI EXTRACTS AND CORTEX MORI EXTRACTS

Both ramulus mori and cortex mori are natural products originated from mulberry trees and both revealed the inhibition effect on tyrosinase activity. The components of two extracts were analysed by thin layer chromatography.

Each extracts (2 μl) prepared in Example 8 and Comparative Example 1, respectively, was dropped on a silica gel thin layer plate (Silica Gef 60 F 254, Merck) and developed thin layer chromatography by using n-butanol: 3N ammonia water: ethanol (5:2:1) mixture as an eluant. The Rf of each component of the extracts was calculated from the formula below:

Rf value=moved distance of sample/moved distance of solvent

The results are shown in Table 6 below.

TABLE 6

Thin layer chromatography of ramulus mori extracts and cortex mori extracts

| | Ramulus Mori extracts | Cortex mori extracts |
|---|---|---|
| $R_f$ | 0.07 | 0.07 |
| | 0.16 | 0.15 |
| | 0.25 | 0.25 |
| | 0.28 | 0.27 |
| | 0.29 | 0.28 |
| | 0.38 | 0.39 |
| | 0.54 | |
| | 0.73 | |
| | 0.83 | |

It was found that the components of ramulus mori extracts were quite different from those of cortex mori extracts.

Formulation 1

An exemplary formula of a skin softener containing ramulus mori extracts is shown below. In the formula, ramulus mori extracts prepared in Example 10 was used.

| Component | Content (%, w/w) |
|---|---|
| ramulus Mori extracts | 0.1 |
| 1,3-butylene glycol | 6.0 |
| glycerin | 4.0 |
| oleyl alcohol | 0.1 |
| polysorbate 20 | 0.5 |
| ethanol | 15.0 |
| preservatives | small quantity |
| benzophenone-9 | 0.05 |
| perfume | small quantity |
| distilled water | residual quantity |
| Total | 100 |

Formulation 2

An exemplary formula of a milk lotion containing ramulus mori extracts is shown below. In the formula, ramulus mori extracts prepared in Example 10 was used.

| Component | Content (%, w/w) |
|---|---|
| ramulus Mori extracts | 0.1 |
| propylene glycol | 6.0 |
| glycerin | 4.0 |
| triethanol amine | 1.2 |
| tocopheryl acetate | 3.0 |
| liquid paraffin | 5.0 |
| squalane | 3.0 |
| macadamia nuts oil | 2.0 |
| polysorbate 60 | 1.5 |
| sorbitan sesquioleate | 1.0 |
| carboxyl vinyl polymer | 1.0 |
| preservatives | small quantity |
| perfume | small quantity |
| distilled water | residual quantity |
| Total | 100 |

Formulation 3

An exemplary formula of a nutrient cream containing ramulus mori extracts is shown below. In the formula, ramulus mori extracts prepared in Example 10 was used.

| Component | Content (%, w/w) |
|---|---|
| ramulus mori extracts | 0.1 |
| vaseline | 7.0 |
| liquid paraffin | 10.0 |
| wax | 2.0 |
| polysorbate 60 | 2.0 |
| sorbitan sesquioleate | 2.5 |
| squalane | 3.0 |
| propylene glycol | 6.0 |
| glycerine | 4.0 |
| triethanol amine | 0.5 |
| carboxy vinyl polymer | 0.5 |
| tocopheryl acetate | 0.1 |
| preservatives | small quantity |
| perfume | small quantity |
| distilled water | residual quantity |
| Total | 100 |

Formulation 4

An exemplary formula of a massage cream containing ramulus mori extracts is shown below. In the formula, ramulus mori extracts prepared in Example 10 was used.

| Component | Content (%, w/w) |
|---|---|
| ramulus Mori extracts | 0.1 |
| propylene glycol | 6.0 |

-continued

| Component | Content (%, w/w) |
|---|---|
| glycerin | 4.0 |
| triethanol amine | 0.5 |
| wax | 2.0 |
| tocopheryl acetate | 0.1 |
| polysorbate 60 | 3.0 |
| sorbitan sesquioleate | 2.5 |
| stearyl alcohol | 2.0 |
| liquid paraffin | 30.0 |
| carboxy vinyl polymer | 0.5 |
| preservatives | small quantity |
| perfume | small quantity |
| distilled water | residual quantity |
| Total | 100 |

Formulation 5

An exemplary formula of a facial pack containing ramulus mori extracts is shown below. In the formula, ramulus mori extracts prepared in Example 10 was used.

| Component | Content (%, w/w) |
|---|---|
| ramulus Mori extracts | 0.1 |
| propylene glycol | 2.0 |
| glycerin | 4.0 |
| carboxy vinyl polymer | 0.3 |
| ethanol | 7.0 |
| PEG-40 hydrogenated castor oil | 0.8 |
| triethanol amine | 0.3 |
| preservatives | small quantity |
| perfume | small quantity |
| distilled water | residual quantity |
| Total | 100 |

EXPERIMENTAL EXAMPLE 6: EVALUATION OF WHITENING EFFECT OF THE COSMETIC PRODUCTS ACCORDING TO THE PRESENT INVENTION

Whitening effect of the cosmetic products according to the present invention was evaluated by practical use test. A nutrient cream prepared according to Formulation 3 with 0.1% of ramulus mori extracts, and a nutrient cream prepared by the same formulation but in which ramulus mori extracts has been substituted by water, were used for the test. Test group consisted of eighty women, whose age being between 30–40 years. The test group was randomly divided into two groups, and let one group apply the proper amount the cream of Formulation 3 on their face after washing their face twice everyday, in the morning and at the evening, while let the other group apply the cream of Comparative Example by the same method. After finishing the practical use test for two months, whitening effect was evaluated with naked eye by examining the enhancement of face condition.

The results are shown in Table 7 below:

TABLE 7

Whitening effect of the cosmetic products of the invention

| | Effective | Somewhat effective | Ineffective | Efficiency |
|---|---|---|---|---|
| Cream of Formulation 3 | 33 | 4 | 3 | 92.5% |
| Cream of Comparative Example | 2 | 3 | 35 | 12.5% |

From the above results, it has been verified that the cosmetic products containing ramulus mori extracts according to the present invention showed excellent whitening effect as compared to the cosmetic products of Comparative Example. No irritation of skin, or the like was revealed on the portion of skin where the product had been applied.

What is claimed is:

1. A cosmetic composition having skin-whitening effect which contains ramulus mori extracts in a cosmetically acceptable vehicle.

2. A cosmetic composition having skin-whitening effect according to claim 1, wherein ramulus mori is young twig of plants belonged to *Morus Genus*.

3. A cosmetic composition having skin-whitening effect according to claim 1, wherein the ramulus mori extracts is obtained by extracting ramulus mori with water, absolute or aqueous lower alcohol containing 1~4 carbons, acetone, ethyl acetate, butyl acetate, chloroform or 1,3-butylene glycol in an extractor equipped with a condenser at 4°~100° C. for 3~20 hours.

4. A cosmetic composition having skin-whitening effect according to claim 1, wherein the ramulus mori extracts is obtained by extracting ramulus mori with water, absolute or aqueous lower alcohol containing 1~4 carbons, acetone, ethyl acetate, butyl acetate, chloroform or 1,3-butylene glycol at 4°~40° C. for 1~15 days.

5. A cosmetic composition having skin-whitening effect according to claim 1, wherein the ramulus mori extracts is contained in an amount of 0.00001~5 % (w/w) of dry weight of the cosmetic composition.

6. A cosmetic composition having skin-whitening effect according to claim 1, wherein the ramulus mori extracts is contained in an amount of 0.001~1 % (w/w) of dry weight of the cosmetic product.

7. A cosmetic composition having skin-whitening effect according to claim 1, wherein the composition is in the form of skin softener, nutrient emulsion (milk lotion), nutrient cream, massage cream, essence, or facial pack.

* * * * *